US011008544B2

(12) United States Patent
Bugeon et al.

(10) Patent No.: US 11,008,544 B2
(45) Date of Patent: May 18, 2021

(54) BIOLOGICAL YEAST, METHOD FOR OBTAINING SAME AND USES THEREOF

(71) Applicant: LESAFFRE ET COMPAGNIE, Paris (FR)

(72) Inventors: Amélie Bugeon, Courpière (FR); Eric Petit, Marquette lez Lille (FR)

(73) Assignee: LESAFFRE ET COMPAGNIE, Paris (FR)

( * ) Notice: Subject to any disclaimer, the term of this patent is extended or adjusted under 35 U.S.C. 154(b) by 129 days.

(21) Appl. No.: 15/114,110

(22) PCT Filed: Apr. 10, 2014

(86) PCT No.: PCT/FR2014/050869
§ 371 (c)(1),
(2) Date: Jul. 26, 2016

(87) PCT Pub. No.: WO2015/118233
PCT Pub. Date: Aug. 13, 2015

(65) Prior Publication Data
US 2017/0002309 A1    Jan. 5, 2017

(30) Foreign Application Priority Data
Feb. 6, 2014  (FR) ..................... 14 50911

(51) Int. Cl.
| C12N 1/16 | (2006.01) |
| A23L 7/104 | (2016.01) |
| A23L 33/14 | (2016.01) |
| C12N 1/18 | (2006.01) |

(52) U.S. Cl.
CPC .......... *C12N 1/16* (2013.01); *A23L 7/104* (2016.08); *A23L 33/14* (2016.08); *C12N 1/18* (2013.01); *A23V 2002/00* (2013.01)

(58) Field of Classification Search
None
See application file for complete search history.

(56) References Cited

U.S. PATENT DOCUMENTS

| 4,414,228 A | * | 11/1983 | Nourigeon | ............ A21D 6/001 426/19 |
| 4,734,283 A | * | 3/1988 | Siren | ............ A21D 2/30 424/439 |
| 5,593,855 A | * | 1/1997 | Lee | ............ C12P 9/00 435/255.21 |
| 5,962,254 A | * | 10/1999 | Saniez | ............ A23J 3/18 426/46 |
| 8,323,717 B2 | * | 12/2012 | Aleid | ............ C12N 1/18 426/549 |
| 2002/0006647 A1 | * | 1/2002 | Veit | ............ C12C 5/004 435/162 |
| 2010/0278965 A1 | | 11/2010 | Boze et al. | |
| 2012/0288587 A1 | | 11/2012 | Cheng et al. | |

FOREIGN PATENT DOCUMENTS

| BE | 421525 A | 5/1937 |
| EP | 0578572 A1 | 1/1994 |
| EP | 0852910 A1 | 7/1998 |
| EP | 1 910 531 B1 | 4/2010 |
| JP | 48-27479 B1 | 8/1973 |
| JP | 6-38745 A | 2/1994 |
| JP | 10-218692 A | 8/1998 |
| JP | 2000-106833 A | 4/2000 |
| WO | 99/10473 A1 | 3/1999 |

OTHER PUBLICATIONS

EPA, 9.13.4 "Yeast Production", AP 42, Fifth Edition, vol. I Chapter 9: Food and Agriculture Industries, available at the EPA at <<https://www3.epa.gov/ttnchie1/ap42/ch09/>, Jan. 1995 (Year: 1995).*
Beck et al. "Recommendations from the group of independent experts on provisions on organic yeast", European Commission: Directorate-General for Agriculture and Rural Development, available online, meeting notes from Jul. 10 and 11, 2008 (Year: 2008).*
Preliminary Research Report dated Oct. 6, 2014, issued by the French Republic National Institute of Industrial Property in corresponding application No. FR 1450911.
Hahn-Hagerdal, B. et al., "Role of cultivation media in the development of yeast strains for large scale industrial use", Microbial Cell Factories, 2005, vol. 4, No. 1, p. 1-16.
Chu, Gyo-Moon et al, "Brewer's yeast efficiently degrades phytate phosphorus in a corn-soybean meal diet during soaking treatment", Animal Science Journal, 2009, vol. 80, No. 4, pp. 433-437.
Garcia-Estepa, R. M. et al., "Phytic acid content in milled cereal products and breads", Food Research International, 1999, vol. 32, No. 3, pp. 217-221.
The New EU Regulation for Organic Food and Farming: (EC) No. 834/2007; Published and edited by IFoam EU Group, Brussels, 2009; 68 pages.
Rao et al.; Isolation and characterization of ethanol-producing yeasts from fruits and tree barks, Lett. Appl. Microbiol. 2008, vol. 47, No. 1, pp. 19-24.

* cited by examiner

*Primary Examiner* — Emily A Cordas
(74) *Attorney, Agent, or Firm* — Sughrue Mion, PLLC

(57) ABSTRACT

The present invention relates to a method for producing yeast. It relates in particular to a method for producing biological yeast, comprising the use of substrates of biological origin, in particular a biological substrate which makes it possible to supplement the nutritional requirements in the yeast in terms of phosphorus.

The method of the present invention makes it possible to obtain biological yeast and biological yeast extracts in accordance with European Union Regulation (EC) 834/2007.

According to the invention, the phosphorus-rich biological composition is obtained by hydrolysis and solubilization of at least one plant substrate of biological origin comprising from 2 to 18 g of phosphorus per kg of product, 60% to 80% of which is in the form of phytic acid. The preferred substrate according to the invention is wheat bran.

13 Claims, No Drawings

BIOLOGICAL YEAST, METHOD FOR OBTAINING SAME AND USES THEREOF

RELATED PATENT APPLICATIONS

The present application is filed pursuant to 35 U.S.C. § 371 as a U.S. National Phase application Ser. No. 15/114,110 of International Patent Application No. PCT/FR2014/050869, which was filed on Apr. 10, 2014, claiming the benefit of priority to French Patent Application No. FR 14 50911 filed on Feb. 6, 2014. The content of each of the aforementioned Patent Applications is incorporated herein by reference in its entirety.

TECHNICAL FIELD OF THE INVENTION

The present invention relates to a method for producing yeast. It relates in particular to a method for producing biological yeast, comprising use of substrates of biological origin, in particular a biological substrate which makes it possible to supplement the nutritional requirements in the yeast in terms of phosphorus. The method of the present invention makes it possible to obtain biological yeast and biological yeast extracts in accordance with European Union Regulation (EC) 834/2007.

Technological Background/Problem to be Solved

In order to multiply, yeast needs carbon and energy sources, such as a mixture of glucose, fructose and sucrose sugars. It also needs nitrogen, phosphorus, oxygen and other trace elements, including inter alia magnesium, sodium, potassium, zinc, copper or else manganese and growth factors including biotin, inositol, pantothenic acid, thiamine, pyridoxine, nicotinic acid or even para-aminobenzoic acid. In the context of the conventional production of yeasts, sugarcane molasses or sugar beet molasses are generally used as a combined carbon and energy source. These molasses provide the yeast with most of its carbon, mineral, trace element and vitamin requirements.

The nitrogen contents of yeast varies from 6% to 9% of the dry matter of the yeast, i.e. from 37% to 56% of proteins. However, the nitrogen provision by the molasses is largely insufficient. Consequently, the provision of nitrogen to the culture medium is usually carried out in the form of hydroxide or other ammonium salts or else urea.

Molasses lacks phosphorus. The phosphorus composition of the yeast, expressed as $P_2O_5$, is generally a third of that of nitrogen, i.e. from 2% to 3% of the dry matter. The phosphorus is generally added in the form of phosphoric acid or salts thereof.

European regulations impose strict orders for the production of biological yeast, whether it is intended for human food or animal feed and whatever the application for which said yeast is intended (bread making, yeast extracts, wine making, etc.).

Thus, only substrates produced according to the biological mode can be used (Regulation (EC) No. 834/2007). However and by special dispensation (Regulation (EC) No. 889/2008 after modification by Regulation (EC) No. 1254/2008), 5% of nonbiological yeast extract or autolysate (YEX) calculated on the basis of the dry matter of the biological substrates are authorized provided that operators are not in a position to obtain yeast extract or autolysate from biological production.

This dispensation to use nonbiological YEX was introduced by the legislator in order to supplement the provisions of nitrogen, phosphorus, vitamins and minerals absolutely required for the production of biological yeast.

Indeed, the industrial manufacture of yeast can be envisaged only if the nutritional requirements of the yeast are perfectly covered.

When the biological substrates used for the manufacture of biological yeast are cane and beet molasses and also a protein source isolated from an agricultural product resulting from biological agriculture, these substrates provide, in sufficient amount, the sugar, the nitrogen and a part of the minerals and vitamins required for growth.

On the other hand, the phosphorus requirement is not met. In this case, the use of the yeast autolysate makes it possible to cover it. However, even by selecting a particularly phosphorus-rich autolysate, the weight limitation of its use only incompletely covers the requirements of an industrial manufacture and, as a result, limits the quality and the regularity thereof.

The provision of a phosphorus-rich substrate produced according to the biological mode would make it possible to solve the above-mentioned problem and to thus produce biological yeast and biological yeast extracts in accordance with European Union Regulations.

The applicant has found that certain phytic acid-rich products of biological origin are, after solubilization and hydrolysis, a source of phosphorus that can be efficiently assimilated by yeast.

SUMMARY OF THE INVENTION

A first subject of the invention is a method for producing biological yeast, comprising the use of carbon, nitrogen and phosphorus sources of biological origins.

The phosphorus source of biological origin according to the invention is a phosphorus-rich purified solution obtained by means of a method comprising at least one step of solubilization and hydrolysis of a phytic acid-rich substrate or a mixture of phytic acid-rich substrates of biological origin.

Another subject of the invention is a purified solution of biological origin which is rich in phosphorus that can be assimilated by yeast.

Another subject of the invention is the use of the phosphorus-rich purified solution of biological origin for producing biological yeast.

Another subject of the invention is a biological yeast in accordance with European Union Regulations.

A subject of the invention is also a biological yeast extract in accordance with European Union Regulations.

DETAILED DESCRIPTION OF THE INVENTION

The first subject of the present invention is a method for producing biological yeast, comprising the use of substrates of biological origins capable of providing all the nutrients required for the growth of the yeast.

These substrates are preferentially molasses as a source of sugars, a source of hydrolyzed biological proteins as a source of nitrogen and at least one phosphorus-rich purified solution as a source of phosphorus.

The method of the invention also comprises the use of other substances required for the growth of the yeast, chosen from those authorized by the European Regulation, such as sodium carbonate, lactic or citric acids and vegetable oils.

The method of the invention uses molasses of biological origin as a source of sugar. According to one form of the invention, the molasses used is chosen from cane molasses and beet molasses. In order to take advantage of their different compositions in terms of minerals and vitamins, it is preferable according to the invention to jointly use cane and beet molasses in a ratio of between 50/50 and 80/20. According to one preferred form of the invention, the cane molasses/beet molasses ratio is between 65/35 and 75/25, and more preferentially close to 70/30.

According to the invention, the biological source of nitrogen is a source of hydrolyzed biological proteins, chosen from rice, pea, potato, wheat, soy, alfalfa, spirulina and gluten proteins.

According to one preferential form of the invention, the biological source of nitrogen is hydrolyzed gluten.

The hydrolysis of the biological source of nitrogen can be carried out using an enzymatic cocktail which makes it possible to have a degree of solubilization of the dry matter close to 80% and a nitrogen yield of 80% to 85%. This enzymatic cocktail comprises a mixture of endoproteases and exopeptidases, preferentially all or part of the mixture NEUTRASE® a neutral, zinc metallo endo-protease from *Bacillus amyloliquefaciens*), ALCALASE® (a serine endopeptidase that consists primarily of subtilisin A), CRISTALASE® (a liquid preparation of purified papain, standardized with sorbitol) and FLAVOURZYME® (a peptidase preparation from *Aspergillus oryzae*). These enzymes, which are non-GMO, are authorized for the manufacture of protein hydrolysates.

According to the invention, the provision of phosphorus is covered by the use of a solution, of biological origin, which is purified and rich in phosphorus. This solution is obtained by solubilization and hydrolysis of a phytic acid-rich plant substrate of biological origin, the phosphorus being released in the form of inorganic phosphate after solubilization and hydrolysis of the phytic acid.

According to the invention, the "phytic acid-rich biological substrate" is intended to mean a plant substrate of biological origin comprising from 2 to 18 g of phosphorus per kg of substrate, 60% to 80% of which is in the form of phytic acid.

The phytic acid-rich substrate according to the invention is chosen from the group of plants listed in table I below:

TABLE I

Total phosphorus contents, phytic phosphorus to total phosphorus ratio and phytase activity of various raw materials (according to Sauvant 2002).

| Name | P (g/kg raw) mean (standard deviation) | Phytic P/total P (%) | Phytase activity (U/kg) | Group of interest |
|---|---|---|---|---|
| Corn gluten | 8.9 (1.5) | 65 | 0 | 1 |
| Fatty rice bran | 16.1 (2.1) | 85 | 120 | 1 |
| Rapeseed | 6.6 (0.9) | 70 | 0 | 1 |
| Rapeseed cake | 11.4 (0.9) | 60 | 10 | 1 |
| Soy cake | 6.2 (0.5) | 60 | 20 | 1 |
| Sunflower cake | 10.1 (1.4) | 85 | 0 | 1 |
| Half-white common wheat middlings | 8.7 (1.4) | 80 | 2590 | 2 |
| Wheat bran | 9.9 (1.1) | 80 | 1770 | 2 |
| Rye | 3 (0.3) | 65 | 5350 | 3 |
| Low-grade common wheat flour | 3.6 | 80 | 3080 | 3 |

As indicated in the table above, certain phytic acid-rich substrates exhibit a more or less marked phytase activity. The phytic acid-rich substrate of biological origin according to the invention will be chosen according to either:

its high phosphorus content (group of interest 1);
its high phosphorus content and its richness in phytase activity (group of interest 2); or
its richness in phytase activity (group of interest 3).

In addition to the phosphorus, essentially present in the form of phytic acid, these compounds also contain proteins or even starch, compounds that are very useful for yeast growth.

For example, the average composition of wheat bran and of soy cake is:
for wheat bran:
  dry matter content: 87% on product as is (TQ)
  phosphorus: approximately 1% (TQ), i.e. approximately 10 g of phosphorus per kg of product, in the form of phytic acid at 80%. Phytase activity 1770 U/kg
  proteins: 15% to 18% (TQ)
  starch: 20% (TQ)
for soy cake:
  dry matter content: 88% to 93% (TQ)
  phosphorus: 0.6% (TQ), (i.e. approximately 6 g of phosphorus per kg) in the form of phytic acid (60%) and of phospholipids. Phytase activity 20 U/kg
  proteins: 41% (TQ).

It is necessary to hydrolyze these compounds in order to release the substances that can be assimilated by the yeast, since neither the phytic acid nor the proteins and the starch can be assimilated as they are by the yeast.

Phytic acid, of chemical formula $C_6H_{18}O_{24}P_6$, consists of an inositol ring and 6 phosphate groups (InsP6). Under the action of a phytase, the phytic acid is hydrolyzed in the form of inorganic monophosphate and of myoinositol phosphates having a lower degree of phosphorylation (InsP5 to InsP1) and free myoinositol in certain cases as described in EP 1 910 531 B1.

The phytase used for this hydrolysis may be endogenous to one of the rich substrates used in the mixture to be hydrolyzed, or exogenous in the case where the mixture of plants to be hydrolyzed is deficient in endogenous phytase activity.

It should be noted that wheat bran does not require the use of exogenous phytase. The solubilization of the phosphorus of wheat bran without recourse to exogenous phytase activity is particularly advantageous since the provision of phytase not derived from GMOs (biological regulation obligation) is difficult.

The mixture of plants, such as those described in table I, can allow the provision of phytase activity even though the plant used might not at first glance be described as phosphorus-rich (substrates of group of interest 3 of table I).

The solubilization and hydrolysis of phytic acid are carried out according to the mode comprising at least the following steps:
  milling the phytic acid-rich biological substrate,
  suspending in water and heating the suspension, and
  enzymatic deactivation.

By way of indication, the milling is carried out using a hammer mill equipped with an 800 μm grill. However, any type of mill can be used.

The suspending in water is carried out in a proportion of from 100 to 250 g and preferably from 160 to 180 g of milled product per kg of final suspension. The suspension is heated at a temperature of between 40 and 50° C. for 5 to 20 hours.

For the enzymatic deactivation, the suspension is brought to a temperature of 90° C. for a period ranging from 15 to 30 minutes, also enabling pasteurization of the substrate.

It is sometimes necessary to add an exogenous phytase to the suspension so as to reinforce or supplement the endogenous phytase activity. In this case, the exogenous phytase is used in a proportion of 15 to 25 g per kg of milled product.

At the end of these treatments, the suspensions are decanted and/or clarified and/or filtered.

In order to maximize the recovery of the solubilized matter, the decanting sludges, the centrifugal clarification sludges or the filtration cakes can be washed, and the washing waters are then combined with the initial supernatant. All of the solutes can then be concentrated.

The analysis of the harvested concentrated supernatants and washing waters shows that 80% to 90% of the phosphorus contained in the initial substrate is solubilized.

According to one preferred mode of the invention, the phytic acid-rich substrate is wheat bran.

In certain cases, the solubilization of the phosphorus can be added to using more conventional treatments of protein hydrolysis (mixture of endo and exopeptidases) and of starch saccharification (use of a mixture of amylase and amyloglucosidase).

Another subject of the invention is the use of a phosphorus-rich purified solution, as described above, in a method for producing yeast, in particular in a method for producing biological yeasts, comprising the use of substrates of biological origin.

The method for producing the yeast of the invention is carried out under the culture conditions normally used for producing conventional yeast, likewise with regard to the operating conditions for recovering, drying and packaging the yeasts produced.

The present invention makes it possible in particular to uncouple the provisions from the main ingredients required for the yeast growth, namely the sugar, nitrogen source, phosphorus source and air. This uncoupling is desired in order to control the final composition of the yeast manufactured.

Another subject of the invention is the biological yeast as produced by means of the method of the invention.

Another subject of the invention is the use of the biological yeast of the invention in the bread making field and the alcohol production field, and more generally for human food and animal feed.

The yeasts of the invention are particularly useful for producing biological yeast extracts.

Another subject of the invention is a biological yeast extract obtained from the biological yeasts of the invention.

The following examples illustrate the invention without limiting the scope thereof.

EXAMPLES

Example 1

Solubilization and Hydrolysis of Gluten

It is known that hydrolysis of plant proteins by a purified protease (of papain or alcalase type) can be improved by adding yeast undergoing autolysis (EP0578572A, US201202888587).

In order to demonstrate the effectiveness of the enzymatic cocktail proposed by the invention, the applicant carried out the following three tests:

Recipe 1: gluten of Blattman origin, biological brewer's yeast in which autolysis has been brought about, papain Recipe 2: gluten of Celnat origin, biological baker's yeast in which autolysis has been brought about, papain (CRISTALASE®), NEUTRASE® and ALCALASE®

Recipe 3: gluten of Celnat and/or Blattman origin, NEUTRASE®, ALCALASE®, FLAVOURZYME®.

Firstly (recipe 1), only biological brewer's yeast in which autolysis has been brought about was used in combination with papain (CRISTALASE®). Next, secondly, and in order to compensate for the loss of proteolytic activities of the brewer's yeast cells, two supplementary enzymes were used (NEUTRASE® and ALCALASE®) in combination with biological baker's yeast in which autolysis has been brought about (recipe 2).

Finally, the papain is replaced with Flavourzyme (mixture of endoprotease and exopeptidase) and the use of biological baker's cream yeast in which autolysis has previously been brought about was abandoned.

The matter balances of these 3 hydrolysis recipes are correlated in table II.

TABLE II

| Overall results of the various gluten hydrolysis recipes used during the biological yeast tests | | | | | |
|---|---|---|---|---|---|
| Recipe | Recipe 1 | Recipe 2 | | Recipe 3 | |
| Raw materials (in kg DM/T nonclarified final hydrolysate) | | | | | |
| Gluten | | | | | |
| nature | Blattman | Celnat | Celnat | Celnat | Blattman |
| DM content | 93.9% | 93.4% | 93.6% | 94.1% | 92.6% |
| concentration | 23 kg DM/T | 103 kg DM/T | 167 kg DM/T | 138 kg DM/T | 152 kg DM/T |
| DM ratio | 50% | 90% | 100% | 100% | 100% |
| Yeast | | | | | |
| nature | Brewer's | Baker's | | | |
| concentration | 23 kg DM/T | 10 kg DM/T | | | |
| DM ratio | 50% | 10% | | | |
| Enzymes (in kg DM/T DM to be hydrolyzed) | | | | | |
| Protein hydrolysis | | | | | |
| Papain | 3.34 kg DM/T | 21.43 kg DM/T | | | |
| Neutrase® | | 19.10 kg DM/T | 3.20 kg DM/T | 4.78 kg DM/T | 4.85 kg DM/T |
| ALCALASE® | | 17.85 kg DM/T | 2.58 kg DM/T | 3.86 kg DM/T | 3.92 kg DM/T |
| FLAVOURZYME® | | | 0.11 kg DM/T | 0.16 kg DM/T | 0.16 kg DM/T |

TABLE II-continued

Overall results of the various gluten hydrolysis recipes used during the biological yeast tests

| Recipe | Recipe 1 | Recipe 2 | Recipe 3 | | |
|---|---|---|---|---|---|
| Solubilization | | | | | |
| Dry matter | | | | | |
| content (kg DM/T supernatant) | 43.0 kg DM/T | 99.0 kg DM/T | 153.3 kg DM/T | 128.2 kg DM/T | 135.5 kg DM/T |
| yield (% of DM involved) | 81% | 73% | 80% | 83% | 79% |
| Nitrogen | | | | | |
| yield (% of N involved) | 86% | 82% | 80% | 84% | 85% |
| Amount of sludge after lab centrifugation 4000 G-10 min (in kg DM/T nonclarified hydrolysate) | | | | | |
| amount | 7 kg DM/T | 31 kg DM/T | 38 kg DM/T | 25 kg DM/T | 29 kg DM/T |
| sludge DMS content | 10% | 28% | 30% | 27% | 28% |

In terms of solubilization of the dry matter implemented, only recipe 2 exhibited a lower effectiveness (73% compared with 80-83%).

In terms of solubilization of the nitrogen, no clear difference is apparent between the three recipes tested. Use of Flavourzyme therefore appears, overall, to effectively replace the use of cream yeast (recycled biological or brewer's yeast, in which autolysis has been brought about beforehand).

Recipe 3 enables a nitrogen yield close to 85%, which is largely sufficient, and a degree of protein degradation of 39% which is quite satisfactory, the degree of degradation being the ratio between the amino nitrogen content of the hydrolysate (resulting from the hydrolysis) and the total nitrogen content of the hydrolysate.

Example 2

Solubilization and Hydrolysis of Wheat Bran and of Soy Cake

The operating conditions of the various treatments applied and also the results obtained are described hereinafter:

Wheat bran:
  milling of the bran. By way of illustration, a hammer mill equipped with an 800 μm grill was used during the pilot tests;
  suspending in water in a proportion of 165 g of milled bran per kg of suspension;
  heating at 40 to 50° C. for 5 to 20 hours;
  no addition of exogenous phytase, the reaction takes place by virtue of the endogenous phytase activity of the bran;
  enzymatic deactivation at 90° C. for 30 minutes.

Soy cake:
  milling of the cake. By way of illustration, a hammer mill equipped with an 800 μm grill was used during the pilot tests;
  suspending in water in a proportion of 165 g of milled cake per kg of suspension;
  heating at 40 to 50° C.;
  addition of exogenous phytase (Sumizyme PHY) at the dose of 20 g per kg of crude cake used, the endogenous phytase activity being virtually zero;
  treatment duration 5 to 20 hours, temperature regulated;
  enzymatic deactivation at 90° C. for 30 minutes.

At the end of these treatments, the bran or cake suspensions are decanted and/or clarified and/or filtered.

In order to maximize the recovery of the solubilized matter, the decanting sludges, the clarifying sludges or the filtration cakes can be washed, and the washing waters are then combined with the initial supernatant. All of the solutes can then be concentrated.

The analysis of the harvested concentrated supernatants and washing waters shows that 80% to 90% of the phosphorus contained in the initial substrate is solubilized.

The use of exogenous phytase for the treatment of the wheat bran does not improve the solubilization/recovery yield.

The solubilization of the wheat bran phosphorus without recourse to exogenous phytase activity is particularly advantageous since the provision of phytase not derived from GMOs (biological regulation obligation) is difficult.

The solubilization of the phosphorus can then be added to by more conventional treatments of bran or cake protein hydrolysis (use of a mixture of endo and exopeptidases) and of wheat bran starch saccharification (use of a mixture of amylase and amyloglucosidase).

By way of example, the implementation of these various treatments makes it possible to prepare clarified hydrolysates of which the compositions are summarized in table III.

Tableau III

Characteristics of the various wheat bran or soy cake hydrolysates obtained after successive treatments in order to hydrolyze the phytic acid then the proteins then the starch

| Characteristic of the clarified juice | | Wheat bran decoction phytic acid hydrolysis | | | Soy cake decoction phytic acid hydrolysis by exogenous enzymes | |
|---|---|---|---|---|---|---|
| | | | + protein hydrolysis | + starch hydrolysis | | + protein hydrolysis |
| Dry matter | g/kg | 51.3 | 81.2 | 81.4 | 83.5 | 116.6 |
| Nitrogen | % DM | 4.9 | 3.8 | 4.0 | 4.2 | 8.3 |
| $P_2O_5$ | % DM | 13.7 | 6.8 | 7.1 | 3.7 | 2.2 |
| Sugar monomer | g/kg | 15.6 | 23.8 | 43.2 | | |

It is particularly interesting to note that the $P_2O_5$/DM contents of the clarified hydrolysates derived from wheat bran are high.

Example 3

Production of Biological Yeast

The various hydrolysates resulting from the treatment of the wheat bran or of the soy cake (example 2) were used for the production of biological yeast, according to a conventional industrial method for producing compressed yeasts.

As a whole, the tests proceeded very well at all levels of the manufacturing cycle tested.

The growth yields observed during the parent yeast stages are comparable to those normally noted with yeast autolysate.

No $P_2O_5$ deficiency was noted within prefermentation or in first generation (G1 parent yeast) (table IV).

The growth yields are very good.

The fermentative activity of this series of tests is overall very satisfactory and equivalent to that of the reference tests. The preservation of the friability of the compressed yeasts produced is good.

In conclusion, the phosphorus resulting from the hydrolysis of the phytic acid contained in the wheat bran, or the soy cake, can therefore indeed be assimilated by the baker's yeast and allows the manufacture of a quality yeast.

TABLE IV

Phosphorus content noted during the production of biological yeast (the phosphorus content is expressed as % $P_2O_5$/yeast dry matter)

| | Wheat bran hydrolysate | Soy cake hydrolysate |
|---|---|---|
| Prefermentation | 5.5 | 4.4 |
| Parent yeast (G1) | 1.8 | 1.8 |
| Commercial yeast (G2) | 1.7 to 2.1 | 1.5 to 1.6 |

The invention claimed is:

1. A method for preparing a biological yeast culture medium, said culture medium comprising carbon, nitrogen and phosphorus sources of biological origins, the phosphorus source being a phosphorus-containing purified solution obtained by hydrolysis and solubilization of at least one phytic acid-rich biological substrate comprising from 2 to 18 g of phosphorus per kg of substrate, 60% to 80% of which is in the form of phytic acid, said method comprising the following steps:

a) milling said phytic acid-rich biological substrate,
b) suspending the product obtained in a),
c) heating the suspension,
d) enzymatic deactivation of the suspension to obtain the phosphorus source,
e) conducting protein hydrolysis on a substrate containing protein to obtain the nitrogen source, and
f) adding a substrate containing molasses to obtain the carbon source, wherein said steps produce a biological yeast culture medium, and wherein said method makes it possible to obtain a biological yeast or biological yeast extract in accordance with European Union Regulation (EC) 834/2007, and wherein said at least one phytic acid-rich biological substrate comprises a phytic acid-rich biological substrate having endogenous phytase, and exogenous phytase is not added in the method.

2. The method as claimed in claim 1, wherein said phytic acid-rich substrate is chosen from the group comprising: corn gluten, fatty rice bran, rapeseed, soy cake, sunflower cake, half-white common wheat middlings, wheat bran, rye, and common wheat flour.

3. The method as claimed in claim 1, wherein the milled substrate is suspended in water in a proportion of from 100 to 250 g of milled product per kg of suspension.

4. The method as claimed in claim 1, wherein the suspension is heated at a temperature of between 40 and 50° C. for 5 to 20 hours.

5. The method as claimed in claim 1, wherein the suspension comprises a phytase.

6. The method as claimed in claim 1, wherein the phytic acid-rich substrate is wheat bran.

7. The method as claimed in claim 1, wherein the solubilization and hydrolysis method further comprises protein hydrolysis and starch saccharification of the phytic acid-rich biological substrate.

8. The method as claimed in claim 1, wherein the substrate containing protein is gluten.

9. The method as claimed in claim 8, wherein the gluten hydrolysis is carried out with an enzymatic cocktail comprising a mixture of endoproteases and exopeptidases.

10. The method as claimed in claim 1, wherein the substrate containing molasses is cane and/or beet molasses.

11. The method as claimed in claim 10, wherein the substrate containing molasses consists of a mixture of cane molasses and beet molasses in a ratio of between 50/50 and 80/20.

12. The method as claimed in claim 1, further comprising the addition of sodium carbonate, lactic or citric acids and vegetable oils to the culture medium.

13. A method for preparing a biological yeast culture medium, said culture medium comprising carbon, nitrogen and phosphorus sources of biological origins, the phosphorus source being a phosphorus-containing purified solution obtained by hydrolysis and solubilization of at least one phytic acid-rich biological substrate comprising from 2 to 18 g of phosphorus per kg of substrate, 60% to 80% of which is in the form of phytic acid, said method consisting of the following steps:
  a) milling said phytic acid-rich biological substrate,
  b) suspending the product obtained in a),
  c) heating the suspension,
  d) enzymatic deactivation of the suspension to obtain the phosphorus source,
  e) conducting protein hydrolysis on a substrate containing protein to obtain the nitrogen source, and
  f) adding a substrate containing molasses to obtain the carbon source, and
  optionally adding an exogenous phytase to the suspension, optionally at least one of decanting, clarifying, and filtering the suspension after said enzymatic deactivation, optionally washing at least one of decanting sludges, clarifying sludges, and filtration cakes resulting from said at least one of decanting, clarifying, and filtering to provide washing waters, optionally combining the washing waters and supernatant resulting from said at least one of decanting, clarifying, and filtering, optionally concentrating the washing waters and supernatant to provide concentrated washing waters and supernatant, and optionally harvesting the concentrated washing waters and supernatant to produce a biological yeast culture medium, wherein said steps produce a biological yeast culture medium, and wherein said method makes it possible to obtain a biological yeast or biological yeast extract in accordance with European Union Regulation (EC) 834/2007.

* * * * *